(12) United States Patent
Greiner et al.

(10) Patent No.: US 7,157,280 B2
(45) Date of Patent: Jan. 2, 2007

(54) NUCLEIC ACIDS CODING FOR VACUOLAR INVERTASES, VEGETAL CELLS AND PLANTS CONTAINING SAID NUCLEIC ACIDS AND THE USE THEREOF

(75) Inventors: Steffen Greiner, Offenbach (DE); Hinrich Harling, Göttingen (DE); Karsten Harms, Grünstadt (DE); Thomas Rausch, Heidelberg (DE); Heiko Rosenkranz, Ludwigshafen (DE)

(73) Assignee: Südzucker Aktiengesellschaft (DE)

( * ) Notice: Subject to any disclaimer, the term of this patent is extended or adjusted under 35 U.S.C. 154(b) by 0 days.

(21) Appl. No.: 10/450,606

(22) PCT Filed: Nov. 21, 2001

(86) PCT No.: PCT/EP01/13523

§ 371 (c)(1),
(2), (4) Date: Dec. 11, 2003

(87) PCT Pub. No.: WO02/50109

PCT Pub. Date: Jun. 27, 2002

(65) Prior Publication Data

US 2004/0199947 A1    Oct. 7, 2004

(30) Foreign Application Priority Data

Dec. 21, 2000    (DE) .............................. 100 63 879

(51) Int. Cl.
*C12N 15/29*    (2006.01)
*C12N 5/14*    (2006.01)
*C12N 15/82*    (2006.01)
*A01H 5/00*    (2006.01)

(52) U.S. Cl. .................. 435/468; 435/320.1; 435/419; 536/23.6; 800/285; 800/286

(58) Field of Classification Search ................ 435/455, 435/419, 468, 471, 483, 320.1; 536/23.6; 800/278, 285, 295, 286, 284
See application file for complete search history.

(56) References Cited

U.S. PATENT DOCUMENTS 5,576,428 A    11/1996    Butler et al.
5,665,579 A    9/1997    Fitzmaurice et al. ........ 435/468

OTHER PUBLICATIONS

Ohyama et al. Plant Cell Physiol. 36(2)369-376. 1995.*
Guo-Qing Tang et al. The Plant Cell. vol. 11, pp. 177-189. Feb. 1999.*
Scholes et al. Planta. vol. 200. pp. 265-272. 1996.*
Klan et al. Plant Physiol. vol. 112:1321-1330. 1996.*
Guo et al. Protein tolerance to radom amino acid change. PNAS. Jun. 22, 2004. p. 9205-9210.*
Mazzolini et al. Assaying synthetic ribozymes in plants: high level expression of a functional hammerhead structure filas to inhibit target gene activity in transiently trsnsformed protoplasts. Plant Molecular Biology. vol. 20. 1992. p. 715-731.*
NCBI Sequence Viewer; X81793—C.rubrum ClN2 mRNA for Intracellular Invertase. Sep. 2, 1997.
R.J. Milling, et al.; "Synthesis of a Vocuolar Acid Invertase in Washed Discs of Storage Root Tissue of Red Beet (Beta Vulgaris L.);" Journal of Experimental Botany, vol. 44, No. 268, pp. 1687-1694, Nov. 1993.
Guo-Qing Tang, et al.; "Antisense Repression of Vacuolar and Cell Wall Invertase in Transgenic Carrot Alters Early Plant Development and Sucrose Partitioning;" The Plant Cell, vol. 11, pp. 177-189, Feb. 1999.
Julie Scholes, et al.; "The Impact of Reduced Vacuolar invertase Activity on the Photosynthetic and Carbohydrate Metabolism of Tomato;" Planta vol. 200, pp. 265-272, 1996.
Akio Ohyama, et al.; "Suppression of Acid Invertase Activity by Antisense RNA Modifies the Sugar Composition of Tomato Fruit;" Plant Cell Physiol. 36(2): 369-376 (1995).
Ellen M. Klann, et al.; "Antisense Acid Invertase (TIV1) Gene Alters Soluble Sugar Composition and Size in Transgenic Tomato Fruit;" Plant Physiol. (1996) 112: 1321-1330.
Peters KF, et al.; "Isolation and Genetic Manipulation of Invertase Genes in Sugarcane;" CSIRO Division of Tropical Crops and Pastures, Brisbane. 1996, pp. 127-129.

* cited by examiner

*Primary Examiner*—Ashwin Mehta
(74) *Attorney, Agent, or Firm*—Dickstein, Shapiro, LLP.

(57) ABSTRACT

The present invention relates to a nucleic acid molecule encoding a vacuolar invertase and its use for modifying the plant saccharose metabolism, in particular in the vacuole of the cell of a plant storage organ. The present invention also relates to a fragment of the nucleic acid molecule, a vector containing the nucleic acid molecule or a fragment thereof, as well as a host cell, in particular a plant cell that contains the nucleic acid molecule or a fragment thereof. The present invention also comprises a transgenic plant, methods for producing a transgenic plant, as well as methods for modifying the saccharose metabolism of a plant, in particular of a plant part.

19 Claims, 5 Drawing Sheets

Vlwit

PAL

After Injury

NUCLEIC ACIDS CODING FOR VACUOLAR INVERTASES, VEGETAL CELLS AND PLANTS CONTAINING SAID NUCLEIC ACIDS AND THE USE THEREOF

FIELD OF THE INVENTION

The present invention describes a nucleic acid molecule that encodes a vacuolar invertase and its use for modifying the plant saccharose metabolism, especially in the vacuole of the cell of a plant storage organ. The present invention furthermore relates to a fragment of the nucleic acid molecule, a vector containing the nucleic acid molecule or a fragment thereof, as well as a host cell, in particular a plant cell that contains the nucleic acid molecule or a fragment thereof. The present invention furthermore comprises a transgenic plant, methods for producing a transgenic plant, as well as methods for modifying the saccharose metabolism of a plant, in particular of a plant part.

BACKGROUND OF THE INVENTION

During the storage of sugar beets (Beta vulgaris), i.e., during the period between harvest and further processing, significant saccharose losses occur, which can be attributed mainly to respiration and the saccharose metabolism. The saccharose loss is associated with a reduction in the quality of the sugar beets, as the content of reducing sugars, such as glucose and fructose, increases (Burba, M., Zeitschrift für die Zuckerindustrie, 26 (1976), 647–658). The saccharose breakdown during the storage of sugar beets comprises as a first metabolic step an enzymatic hydrolysis as a result of a vacuolar invertase. Vacuolar and/or cell wall-bound invertase isoforms are also induced by de novo injuries to beet tissue (Milling et al., J. Exp. Bot., 44 (1993), 1687–1694). This means that injuries also result in a saccharose hydrolysis, particularly in order to provide hexoses necessary for wound respiration and the wound-activated oxidative pentaphosphate (OPP) cycle. A precise analysis as to which invertase isoforms are involved in the wound reaction has not been performed, however. Understanding the regulation and the role of the individual invertase isoforms in the injured sugar beet tissue is critical, however, for being able to manipulate the expression of the individual isoforms, especially considering the substantial saccharose losses during the storage period.

BRIEF SUMMARY OF THE INVENTION

The present invention is therefore based on the technical problem of providing methods and means enabling the production of plants, in particular sugar beets, with a modified saccharose metabolism. The specific modification of the vacuolar saccharose metabolism in the plant cell, in particular in a vacuole of this cell, therefore remains an essential basic prerequisite for providing plants, particularly sugar beets, with improved storage stability.

DETAILED DESCRIPTION OF THE INVENTION

Figure 1:
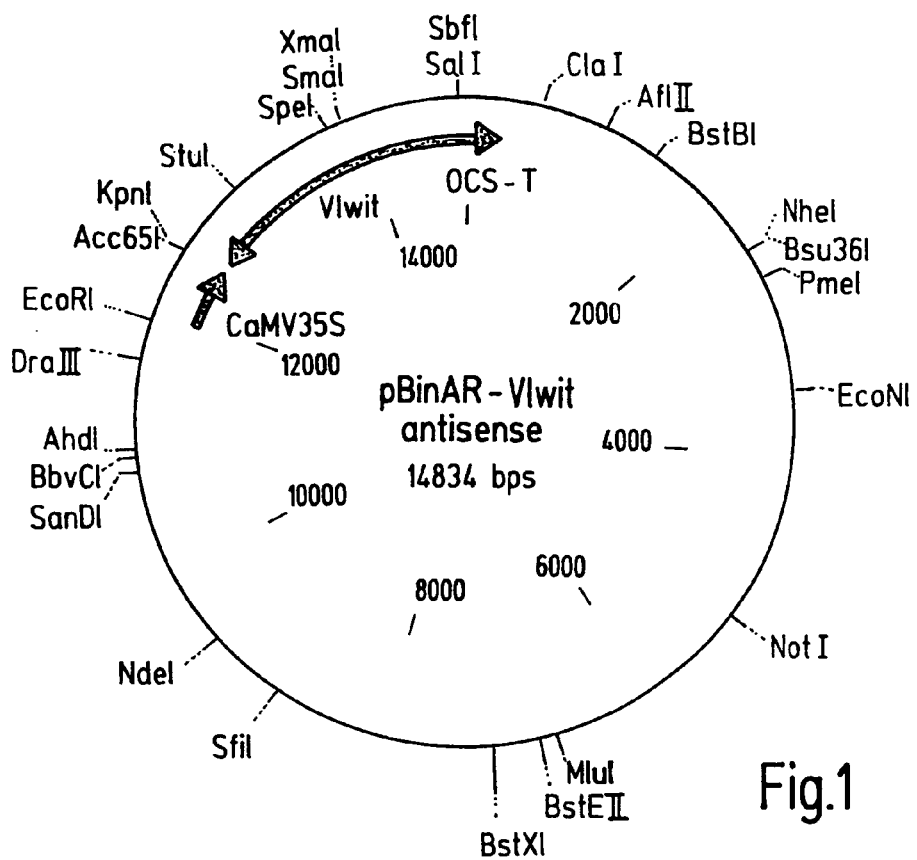
FIG. 1 shows an antisense construct according to the invention with the nucleotide sequence according to the invention, the entire VIwit cDNA sequence being SEQ ID No. 2.

According to the invention, the technical problem was solved by identifying and characterizing a plant gene, which encodes a wound-induced vacuolar invertase (VIwit), and the encoded protein. By specifically modulating the activity, in particular by turning off or inactivating this vacuolar invertase induced by injury, saccharose losses can be reduced during storage or after injury. According to the invention, it was demonstrated for the first time that the activity of a plant vacuolar, wound-induced invertase is inhibited by a corresponding antisense construct. According to the invention, it was shown that the saccharose breakdown induced by injury is caused by a single, defined, and specific vacuolar invertase isoform, VIwit. According to the invention, this isoform was cloned. Different segments of the cDNA sequence provided according to the invention may be used for constructing antisense constructs, sense constructs, sense constructs for co-suppression and for hairpin gene constructs according to Smith et al. (2000 Nature 407, 319–320) for turning off the activity of this wound-induced vacuolar invertase.

According to the invention, a preferably isolated and completely purified nucleic acid molecule is provided, selected from the group consisting of:

a) a nucleic acid molecule with a nucleotide sequence shown in SEQ ID No. 1, 2, 3 or in SEQ ID No. 5 or fragment thereof;

b) a nucleic acid molecule with a sequence encoding a protein with the biological activity of an invertase and with a sequence shown in SEQ ID No. 4 or in SEQ ID No. 6, or a fragment thereof;

c) a nucleic acid molecule complementary to a nucleic acid molecule according to a) to b), or a fragment thereof;

d) a nucleic acid molecule available by substitution, addition, inversion and/or deletion of one or more bases of a nucleic acid molecule according to a) to c);

e) a nucleic acid molecule that hybridizes, for example, due to the degeneration of the genetic code, with a nucleic acid molecule according to a) to d) or a fragment thereof.

A nucleic acid molecule or a nucleic acid may be a DNA sequence, for example, cDNA or a genomic DNA sequence, or an RNA sequence, for example, a mRNA sequence, in particular from the sugar beet, *Beta vulgaris*. The nucleic acid molecule or the nucleic acid preferably is available in isolated and purified form.

The invention also comprises modified nucleic acid molecules available, for example, by substitution, addition, inversion and/or deletion of one or more bases of a nucleic acid molecule according to the invention, in particular within the encoding sequence of a nucleic acid, i.e., also nucleic acid molecules that that may be called mutants, derivatives, or functional equivalents of a nucleic acid molecule according to the invention. Such manipulations of the sequences are performed, for example, in order to specifically modify the amino acid sequence encoded by a nucleic acid. Nucleic acids that encode modified vacuolar invertases may be used, among other things, for transforming agriculturally used plants in order to produce transgenic plants. Specific sequence modifications also may have the goal of providing suitable restriction site or to remove unnecessary restriction sites. In the process, the nucleic acid molecules according to the invention are inserted into plasmids and are subjected, using standard methods, to the microbiology/molecular biology of a mutagenesis or sequence modification by recombination. For example, methods for in vitro mutagenesis, primer repair methods, as well as restriction and/or ligation methods are suited to bring about insertions, deletions, or substitutions, such as transitions and transversions (cf. Sambrook et al., 1989, Molecular Cloning: A Laboratory Manual, 2nd edition (1989), Cold Spring Harbor Laboratory Press, New York, USA). Sequence modifications also may be achieved by the attachment of natural or synthetic nucleic acid sequences. Examples of synthetic nucleic acid sequences are adaptors or linkers, which are added, among other things, also for linking nucleic acid fragments to these fragments.

The present invention also comprises nucleic acid molecules that hybridize with one of the previously described nucleic acid molecules according to a) to d). The expression "nucleic acid molecule that hybridizes with one of the previously described nucleic acid molecules according to a) to d)" used in connection with the present invention means a nucleic acid molecule or a nucleic acid which hybridizes with a nucleic acid molecule or nucleic acid according to a) to d) under moderately stringent conditions. The hybridization, for example, may take place with a radioactive gene probe in a hybridization solution (25% formamide; 5×SSPE; 0.1% SDS; 5×Denhardt solution; 50 µg/ml herring sperm DNA; with respect to composition of individual components, cf. Sambrook et al., Molecular Cloning: A Laboratory Manual, 2nd edition (1989), Cold Spring Harbor Laboratory Press, New York, USA) for 20 hours at 37° C. Unspecifically bound probe is then removed by repeated washing of the filters in 2×SSC/0.1% SDS at 42° C. Preferably the filters are washed with 0.5×SSC/0.1% SDS, especially preferably with 0.1×SSC/0.1% SDS at 42° C. In a preferred embodiment, these nucleic acid molecules have at least 60%, preferably at least 80%, 85%, 90%, 95%, 98%, and especially preferably at least 99% homology (identity) at the nucleic acid level with respect to each other.

The present invention also comprises nucleic acid molecules that encode a polypeptide or protein with the activity of a vacuolar invertase whose sequence has at least 40%, preferably at least 60%, especially preferably at least 70%, 80%, 90%, 95%, especially 99% homology with a polypeptide or protein that is encoded by a nucleic acid with a sequence shown in SEQ ID No. 1,2,3 or in SEQ ID No. 5.

In connection with the invention, the expression "at least 40%, preferably at least 60%, especially preferably at least 70%, 80%, 90%, 95%, especially 99% homology" refers to a sequence match at the amino acid level that can be determined using known methods, for example, computer-based sequence comparisons (Basic local alignment search tool, S. F. Altschul et al., J. Mol. Bio. 215 (1990), 403–410).

The term "homology", known to one skilled in the art, designates the degree of relationship between two or more polypeptide molecules determined by the match between the sequences, whereby a match may be both an identical match as well as a conservative amino acid exchange. The percentage of "homology" is derived from the percentage of matching regions in two or more sequences with consideration of gaps or other sequence peculiarities.

The expression "conservative amino acid exchange" means the exchange of an amino acid residue for another amino acid residue, whereby this exchange does not result in a change of the polarity or charge at the position of the exchanged amino acid, for example, the exchange of a non-polar amino acid residue for another non-polar amino acid residue. Conservative amino acid exchanges in connection with this invention include for example: G=A=S, I=V=L=M, D=E, N=Q, K=R, Y=F, S=T, G=A=I=V=L=M=Y=F=W=P=S=T.

The homology between polypeptide molecules related to each other can be determined using known methods. As a rule, special computer programs with algorithms taking into account the special requirements are used. Preferred methods for determining homology first generate the greatest match between studied sequences. Computer programs for determining the homology between two sequences include, for example, the GCG program suite, including GAP (Devereux, J., et al. Nucleic Acids Research, 12 (12) (1984), 387; Genetics Computer Group University of Wisconsin, Madison (Wis.)); BLASTP, BLASTN, and FASTA (Altschul, S. et al., J. Molec Bio 215 (1990), 403–410). The BLASTX program is available from the National Centre for Biotechnology Information (NCBI) and from other sources (Altschul S., et al., BLAST Manual, NCB NLM NIH Bethesda, MD 20894; Altschul, S. et al., J. Mol. 215 (1990), 403–410). The known Smith Waterman algorithm also can be used to determine homology.

Preferred standard parameters for the amino acid sequence comparison include, for example: Algorithm: Needleman and Wunsch, J. Mol. Biol 48 (1970), 443–453; Comparison matrix: BLOSUM 62 by Henikoff and Henikoff, Proc. Natl. Acad. Sci. USA, 89 (1992),10915–10919; Gap penalty: 12; Gap length penalty: 4; Similarity threshold: 0.

The GAP program also is suitable for using the previously described parameters.

In addition, other algorithms, gap opening values, gap extension values, and comparison matrices may be used, including those described in the program handbook of the Wisconsin Suite, version 9 (September 1997). The selection of programs depends both on the comparison to be performed and whether the comparison is performed on sequence pairs, in which case GAP or Best Fit are preferred, or whether it is performed on a sequence and an extensive sequence database, in which case FASTA or BLAST are preferred.

The present invention also relates to a preferably isolated and completely purified protein that can be obtained by expression of a nucleic acid molecule according to the invention or fragment thereof in a host cell. The protein preferably has the same vacuolar invertase properties as the protein that is encoded by a nucleic acid molecule with a sequence shown in SEQ ID No. 1, 2, 3 or SEQ ID No. 5. In order to determine the activity of such a protein, the saccharose cleavage experiments described in Example 6 may be performed.

In connection with the present invention, the expressions "with the biological activity of an invertase" and "activity of a vacuolar invertase" mean that a polypeptide or protein is able to cleave saccharose or glucose under suitable conditions in vitro or in vivo, for example, in the test described in Example 6 for determining the invertase activity.

The present invention also comprises isolated and completely or partially purified monoclonal or polyclonal antibodies or their fragments that react with a protein according to the invention specifically or with such an affinity that, for example, a detection of this protein is possibly.

The invention furthermore relates to a construct containing a nucleic acid according to the invention or a fragment thereof under control of expression regulation elements. In connection with the present invention, a "construct", which may also be called a vector herein, means the combination of a nucleic acid according to the invention or a fragment thereof with at least one additional nucleic acid element, for example, a regulator element. Examples of such regulator elements are constitutive or inducible promoters, such as the E.coli promoter araBAD (Carra and Schlief, EMBO J., 12 (1993), 35–44) for expression in bacteria, the yeast promoter PMA1 (Rentsch et al., FEBS Lett., 370 (1995), 264–268) for expression in fungal systems, and the viral CaMV35S promoter (Pietrzak et al., Nucl. Acids Res., 14 (1986), 5857–5868) for expression in plants.

In particular, storage-organ-specific promoters of the beet are used according to the invention, so that the nucleic acid according to the invention is expressed in a desired target organ, in particular in the beet organ. Naturally, time-, development-, or other tissue-specific regulator elements may be used also. An especially preferred embodiment comprises the use of wound-activated promoters of the beet, so that the nucleic acid according to the invention is only expressed in the case of an injury.

In addition, the nucleic acid or fragment may be provided with a transcription termination signal. Such elements have been described already (cf., for example, Gielen et al., EMBO J., 8 (1984), 23–29). The transcription start and termination regions may be both native (homologue) or foreign (heterologue) with respect to the host organism. The sequence of the transcription start and termination regions may be of synthetic or natural origin or may contain a mixture of synthetic and natural components. In an especially preferred embodiment of the invention, the construct is a plasmid.

The nucleic acid or fragment may be present in the construct, in particular in a plasmid, both in antisense as well as in sense orientation to the regulator element(s). If the nucleic acid according to the invention or its fragment are present, for example, in sense orientation to the at least one regulator element, for example, a promoter, it may inhibit or reduce the endogenous vacuolar invertase activity by way of co-suppression effects, especially after transformation and integration, also with higher number of copies, into the genome. If the nucleic acid or fragment is present in the construct in antisense orientation to the at least one regulator element, the construct may be inserted, for example, into the genome of a plant host cell and may lead to a suppression of the formation of the plant's own vacuolar invertase. The term "genome" here means the genetic makeup located both in the mitochondria, plastids, or nucleus of a cell.

A preferred embodiment of the present invention therefore comprises a construct that includes a nucleic acid according to the invention or a fragment thereof in antisense orientation to a promoter, whereby the expression of a vacuolar invertase is inhibited in a host cell containing the construct. The nucleic acid fragment hereby preferably includes fragments with a minimum length, which enable the hybridization to endogenous invertase mRNA or DNA, for example, at least 10 nucleotides, preferably at least 50 nucleotides, especially preferably at least 200 nucleotides. The construct that contains a nucleic acid according to the invention or a fragment thereof can be inserted into a host cell and can be transcribed there into a non-translatable RNA (antisense RNA) that is able, by binding to an endogenous gene for a vacuolar invertase or to the mRNA transcribed from it, to inhibit the expression of this endogenous gene.

Another preferred embodiment of the invention relates to a construct that contains a nucleic acid according to the invention or a nucleic acid fragment according to the invention in sense orientation to a regulator element, for example, a promoter, which is followed by another, identical or different nucleic acid according to the invention or another identical or different nucleic acid fragment according to the invention in antisense orientation to it. This arrangement enables the formation of a double-strand RNA able to induce the breakdown of the endogenous RNA.

In another preferred embodiment of the invention, a construct is provided that contains a nucleic acid according to the invention in sense orientation to a regulator element, for example, a promoter. The insertion of such a construct is able to inhibit or reduce the transcription of an endogenously present gene for the vacuolar invertase via the co-suppression effect. This method has been described, for example, by Napoli et al. (The Plant Cell (1990), 2, 279 to 289) or in U.S. Pat. Nos. 5,034,323, 5,231,020, and 5,283,184. Such a sequence arranged in sense orientation also may be used in one embodiment of the invention as a fragment with the minimum lengths mentioned for the previously mentioned antisense fragments.

In another embodiment according to the invention provides that the endogenously present gene or its two alleles of the vacuolar invertase are deactivated or modified in their activity by a mutation of this gene or of the alleles. This may be accomplished, for example, by transposon-induced mutagenesis or homologue recombination using exogenously inserted nucleic acids according to the invention.

Finally, it is also possible according to the invention to inhibit the expression of endogenous vacuolar invertase genes with catalytic RNA molecules or ribozymes; and according to this embodiment, it may be provided that ribozyme sequences are integrated within antisense RNA sequences according to the invention of this invention in order to obtain an RNA-cleaving activity. The production and use of such target-specific ribozymes are described, for example, by Haseloff et al. (Nature (1988), 334, 585 to 591).

The previously mentioned constructs for the modification, in particular repression, inhibition, or suppression, of endogenously present activity of the invertase or invertase gene must not necessarily contain completely identical, full length nucleic acids according to the invention. Rather, it may be sufficient in many embodiments that the nucleic acids used according to the invention, be it during the production of antisense constructs or co-suppression constructs, contain only fragments, i.e., partial sequences, of the complete sequence according to the invention for the vacuolar invertase. The same is true for the degree of identity, which may well be lower, in particular significantly lower than a 100% identity.

Suppression of the expression of the wound-induced vacuolar invertase isoform is achieved according to the invention also with antisense constructs, sense constructs, or hairpin constructs (Smith et al. (2000 Nature 407, 319–320)). In a preferred embodiment, these constructs are cloned using the entire VIwit cDNA sequence (SEQ ID No. 2) or selected regions thereof (SEQ ID No. 1 or 3). In one embodiment, each construct can be brought to expression under the control of the CaMV 35S promoter; in another embodiment under the control of a wound-induced promoter, or in yet another embodiment under the control of a beet-specific promoter. Sequence sections of, for example, at least 10 nucleotides, preferably at least 50 nucleotides, especially preferably at least 200 nucleotides, are used for the antisense and sense constructs.

For the production according to the invention of hairpin constructs according to Smith et al. (2000 Nature 407, 319–320), preferably sequence sections of, for example, at least 10 nucleotides, preferably at least 50 nucleotides, especially preferably at least 200 nucleotides of the VIwit isoform according to the invention are ligated on the 3' side with either a spacer DNA or, in a preferred embodiment, with an intron. Then the sequence that is complementary to the first sequence section is ligated to this on the 3' side in antisense orientation. The intron or spacer sequences used in the aforementioned hairpin construction are here called additional hairpin sequences.

In another preferred embodiment of the invention, the plasmid contains a replication signal for *E. coli* and/or yeast, and a marker gene that permits a positive selection of the host cells transformed with the plasmid. If the plasmid is inserted into a plant host cell, additional sequences, which are known to one skilled in the art, may be required, depending on the insertion method. If the plasmid, for example, is a derivative of the Ti or Ri plasmid, the nucleic acid to be inserted or the fragment thereof must be flanked by T-DNA sequences that enable the integration of the nucleic acid or of the fragment thereof into the plant genome. The use of T-DNA for the transformation of plant cells has been extensively studied and has been described, for example, in EP 120 516; in Hoekema, The Binary Plant Vector System, chapter V (1985), Offset-drukkerij Kanters B. V. Ablasserdam; in Fraley et al., Crit. Rev. Plant. Sci., 4 (1985), 1–46, and in An et al., EMBO J., 4 (1985), 277–287. Once the inserted nucleic acid or fragment thereof is integrated into the genome, it is usually stable there and is also preserved in the progeny of the originally transformed cell.

The sequence integrated in the genome also may include a selection marker that provides the transformed plant cells with resistance to a biocide or an antibiotic, such as kanamycin, G418, bleomycin, hygromycin, or phosphinotricin. The used marker permits the selection of transformed cells versus cells without the transformed DNA.

According to the invention, the vector may be, for example, a plasmid, cosmid, bacteriophage, virus, or liposome.

The invention thus also provides a host cell containing a nucleic acid according to the invention, in particular a nucleic acid with a sequence shown in SEQ ID No. 1, 2, 3 or a nucleic acid with a sequence shown in SEQ ID No. 5, or a fragment thereof, or a construct containing a nucleic acid according to the invention or a fragment thereof. The host cell according to the invention may be a bacterium or a yeast, insect, mammal, or plant cell.

The present invention furthermore relates to a transgenic plant containing in at least one of its cells a nucleic acid according to the invention that encodes a protein with the activity of an, in particular vacuolar, invertase or a fragment thereof, or a construct according to the invention. The transgenic plants may be plants of different species, genera, families, orders, and classes, i.e., both monocotyle as well as dicotyle plants, as well as algae, mosses, ferns, or gymnosperms. Transgenic plants also may include calli, plant cell cultures, as well as parts, organs, tissues, and harvest or propagation materials of these plants. In the present invention, the transgenic plants are in particular tobacco, potato, tomato, sugar beet, sugar cane, soybean, coffee, pea, bean, cotton, rice, or maize plants.

In connection with the present invention, the expression "in at least one of its cells" means that a transgenic plant contains at least one cell, but preferably a plurality of cells, that contain one or more nucleic acids according to the invention or a fragment thereof or a construct according to the invention which have been integrated in a stable manner. The nucleic acid or a fragment thereof or a construct according to the invention may be integrated both in the nucleus of the cell or in the mitochondrial or plastid genome. The nucleic acid, fragment, or construct preferably is integrated in a location of the cell that does not correspond to its natural position, or is integrated with a number of copies and/or in an orientation that does not correspond to the naturally occurring number of copies and/or orientation.

The present invention also relates to a method for producing a transgenic, preferably fertile plant that comprises the following steps:

Insertion of a nucleic acid according to the invention, in particular of a nucleic acid with a sequence shown in SEQ ID No. 1, 2, 3 or a nucleic acid with a sequence shown in SEQ ID No. 5, or a fragment thereof, or a construct containing a nucleic acid according to the invention or a fragment thereof, into a plant cell; and, Regeneration of a preferably fertile plant from the transformed plant cell, whereby at least one cell of this plant is transgenic, i.e., contains a nucleic acid according to this invention integrated in a stable manner and preferably expresses it, i.e., transcribes the integrated nucleic acid to RNA. The resulting plant preferably has a reduced invertase activity in at least one of its vacuoles, and, associated with this, an increased saccharose stability in the vacuole.

A number of methods are available for inserting a nucleic acid into a plant cell. Most of these methods require that the nucleic acid to be inserted is present in a construct, such as a vector. Vectors, for example, plasmids, cosmids, viri, bacteriophages, shuttle vectors, etc., are known. Vectors often comprise functional units for stabilizing the vector in a host cell and for enabling its replication in it. Vectors may also contain regulator elements with which the nucleic acid is functionally bonded and which enable the expression of the nucleic acid.

In addition to the transformation using agrobacteria, for example, *Agrobacterium tumefaciens*, there are numerous other methods available. These methods include the fusion of protoplasts, microinjection of DNA, electroporation as well as biolistic methods and virus injection methods. In contrast to transformation using agrobacteria, injection and electroporation do not per se have any special requirements for the vector. Simple plasmids, such as, for example, pUC derivatives, can be used. However, if whole plants are to be regenerated from such transformed cells, the presence of a selectable marker gene is advantageous.

Then whole plants can be regenerated from the transformed plant cells in a suitable medium potentially containing antibiotics or biocides for selection. The resulting plants then can be tested for the presence of the inserted DNA. The transformed cells grow within the plants in the usual manner (cf. McCormick et al., 1986, *Plant Cell Reports*, 5, 81–84). These plants can be grown as usual and can be crossed with plants having the same transformed genetic traits or other genetic traits. The resulting hybrid individuals demonstrate the corresponding phenotypic properties.

The present invention furthermore relates to a method for the modification of the saccharose metabolism in vacuoles of a plant, in particular the modification in vacuoles of a cell of a storage organ of the sugar beet, whereby a nucleic acid according to the invention, in particular a nucleic acid with a sequence shown in SEQ ID No. 1, 2, 3 or a nucleic acid with a sequence shown in SEQ ID No. 5, or a fragment thereof, are inserted into a plant cell and/or a plant, and then a whole plant is regenerated, whereby in at least one of its cells an expression, i.e., in particular transcription and translation, of the transformed nucleic acid can take place so that a plant with a saccharose breakdown that is reduced in comparison to non-transformed plants in at least one of its vacuoles is obtained.

In order to bring about a modification according to the invention of the properties of the vacuolar saccharose metabolism of a plant, both an antisense formulation, a ribozyme formulation, a double-strand RNA formulation, but also a knock-out formulation or co-suppression formulation may be used. For example, the invention relates to modifications of the saccharose metabolism in the vacuole of a plant, within the context of which the endogenous activity of an invertase is inhibited by antisense expression. In addition, a co-suppression, for example, by inserting several gene copies or constructs containing the nucleic acid sequence isolated according to the invention under the control of a strong constitutively or tissue- and/or time-specifically expressing promoter. Such effects inhibiting the endogenously present invertase activity can be achieved according to the invention by transformation of plant cells with antisense constructs and/or by integration of several sense constructs in order to achieve a co-suppression effect. Naturally, the activity of endogenously present vacuolar invertase genes also can be inhibited via the nucleic acids according to the invention by, for example, transposon-induced insertion into the endogenously present nucleic acid and/or by homologue recombination via homologous recombination.

The present invention furthermore relates to the use of the nucleic acids according to the invention for modifying the saccharose metabolism of plants, in particular, in vacuoles of their storage organs.

The nucleic acids according to the invention, in particular a nucleic acid with a sequence shown in SEQ ID No. 1, 2, 3 or a nucleic acid with a sequence shown in SEQ ID No. 5 also may be used for isolating homologous sequences from bacteria, fungi, plants, animals and/or humans. In order to be able to search for homologous sequences, first gene banks must be created, for example, genomic banks or cDNA banks. With the help of a probe that contains parts of the previously mentioned nucleic acids, sequences then can be isolated from the gene banks. After identification and/or isolation of the corresponding genes, DNA and amino acid sequences can be determined, and the properties of the proteins encoded by these sequences can be analyzed.

The nucleic acids according to the invention also can be used to study the expression of a vacuolar invertase according to the invention in prokaryotic and/or eukaryotic cells. If the previously described nucleic acids, are inserted, for example, into prokaryotic cells, such as bacteria, a RNA sequence, translatable by bacteria, is formed. These bacteria cells therefore can be used for studies of the properties of a vacuolar invertase as well as of its substrates and reaction products. According to the invention, the nucleic acids according to the invention can be used, under control of a regulator element, in antisense direction for inhibiting the expression of an endogenous invertase in prokaryotic and/or eukaryotic cells. Another possible use of these nucleic acids is the production of transgenic crop plants.

The sequence protocol includes:

SEQ ID No. 1 shows a partial cDNA sequence (comprising 686 nucleotides) of the VIwit gene from *Beta vulgaris*.

SEQ ID No. 2 shows the complete cDNA sequence (comprising 2,337 nucleotides) of the VIwit gene from *Beta vulgaris*.

SEQ ID No. 3 shows the encoded region (comprising 1,938 nucleotides) of SEQ ID No. 2.

SEQ ID No. 4 shows the complete amino acid sequence (comprising 645 amino acids and derived from SEQ ID No. 3) of the VIwit protein.

SEQ ID No. 5 shows the partial sequence (comprising 7,564 nucleotides) of the genomic VIwit clone of *Beta vulgaris*.

SEQ ID No. 6 shows a partial amino acid sequence (derived from SEQ ID No. 5 and comprising 284 amino acids) of the VIwit protein according to the invention (corresponds to positions 140 to 423 of SEQ ID No. 4).

SEQ ID No. 7 and 8 show the primers of *Beta vulgaris* used for amplification and cloning.

SEQ ID No. 9 and 10 show the primers of *Beta vulgaris* used to produce antisera directed against the N-terminal protein domain.

Other advantageous embodiments can be derived from the secondary claims.

The following examples and associated figures will explain the invention in further detail:

EXAMPLE 1

Plant Material

The diploid *Beta vulgaris* L. inbred line VV-I/ZR 10676 (KWS Saat AG, Einbeck, Germany) was cultivated under field conditions until bloom (i.e., 66 weeks following sowing). The beets were harvested from the soil in November and stored at 4°C. until April, and then were sown again. For the injury experiments, 24-week-old plants were harvested and stored for 3 months at 6°C. After the plant material had been brought to room temperature, the beet body was decapitated i.e., separated from its stalk. Using a cork drill, tissue cylinders with a diameter of 2 cm were removed from the cortex (4 cylinders per beet body). Immediately after this, the tissue cylinders were cut into slices with a set of fixed razor blades (spaced 2 mm apart). The slices were incubated for different periods of time in a humid atmosphere at room temperature.

EXAMPLE 2

Cloning of cDNA Sequence and Genomic DNA Sequence of the Sugar Beet VI Isoform

After 3 days, RNA was isolated from injured beet tissue. The RNA was amplified with the help of the RT-PCR method using the VIwit-sense primer (SEQ ID No. 7) with the sequence 5'-ATGGTI(G/C)C(G/T)GA(C/T)C(A/G)(A/T)TGGTA(C/T)GA-3' (I=inosit) and the VIwit-antisense primer (SEQ ID No. 8) with the sequence 5'-TC(A/G)(G/C)T(A/G)TC(A/T)G(A/T)(C/T)TC(A/C/T)CCAA(C/T)CCA-3', whereby a partial VIwit cDNA (SEQ ID No. 1) was obtained. Reverse MMLV transcriptase was hereby used for the synthesis of the first strand. With the help of the partial cone, a complete cDNA (SEQ ID No. 2) for VIwit (Vacuolar Invertase, wound induced in tap roots) was cloned.

All PCR products were cloned in the Bluescript SK+ vector (Stratagene, Heidelberg, Germany) and sequenced in both directions. The partial cDNA was used as a matrix for synthesizing gene-specific biotinylated probes according to the method by Löw and Rausch (in: A laboratory guide to biotin-labelling in biomolecule analysis (Ed.: Meier, T. and Fahrenholz, F.), 1996, pages 201–213, Birkhäuser Verlag, Basel).

By screening a genomic database that had been generated with the help of the Lambda-ZAP-XhoI-Partial-Fill-In vector kit (Stratagene, Heidelberg, Germany) (Lehr et al., Plant Mol. Biol., 39 (1999), 463–475), genomic clones of the VIwit gene were isolated (SEQ ID No. 5).

EXAMPLE 3

RNA Blot and Southern Blot Analyses

Total RNA was extracted, as described by Logemann et al. (Analyt. Biochem., 163 (1987), 16–20). The total RNA was separated on a 1.4% agarose gel containing 2% formaldehyde, whereby for each track 20 μg of RNA were applied. After capillary transfer to a nylon membrane (Duralon; Stratagene, Heidelberg, Germany) and UV cross-linking, the blots were hybridized with gene-specific probes.

Genomic DNA was isolated from sugar beet leaves according to the method by Murray and Thompson (Nucl. Acids Res., 8 (1980), 4321–4325). After cleavage with restriction enzymes BglII, EcoRV, and XbaI, 10 μg of RNA were separated on a 0.7% agarose gel and were then transferred to a nylon membrane. The blots were hybridized using the same probes as previously described.

EXAMPLE 4

Production of Antisera

To detect the VIwit protein, an antiserum against the N-terminal protein domain was produced. For this purpose, the partial VIwit cDNA (SEQ ID No. 1) was amplified with two primers that contained the sequences 5'-GCCGAATC-GAGCTCATAAATGGTGTTTGGACAGG-3' (SEQ ID No. 9) or 5'-GCCGTTAGAAGCTTAGCCGAGGTATC-CAACC-3' (SEQ ID No. 10) (whereby these sequences correspond to the amino acid sequences INGVWTG or GLDTSA). The primers contained a restriction site for the restriction enzyme SacI or HindIII respectively. After cleavage with SacI and HindIII, the PCR products were cloned specifically into the pQE30 vector (Qiagen, Hilden, Germany). After insertion into *E.coli* strain M15(pREP4), the N-terminal VIwit domain was overexpressed in this strain and then purified using Ni-NTA affinity chromatography. The purified protein was used to produce a polyclonal antibody in rabbits.

EXAMPLE 5

Immunoblot Analysis

The immunoblot analysis was performed according to the method by Weil and Rausch (Planta, 193 (1994), 430–437), whereby, however, 5% dry milk powder was used in place of BSA for blocking, and the immunoblots were developed using the SuperSignal®-West Dura detection kit (Pierce, Rockford, USA). It was found that with control blots the antiserum to VIwit demonstrated no cross-reactivity with other invertase isoforms, for example, cell wall invertases.

EXAMPLE 6

Determination of the Activity of Vacuolar Invertase

To determine the VIwit activity, tissue was extracted in 30 mM MOPS, pH 6.0, 250 mM sorbitol, 10 mM $MgCl_2$, 10 mM KCl, and 1 mM PMSF. After 10 minutes of centrifugation (6,500×g, 4° C.), the acetone was added to the supernatant (80% final concentration) to precipitate the protein. The protein pellet was suspended in test buffer without saccharose. Aliquots were tested for the activity of the soluble, acidic invertase (VI) in test buffer, whereby the test buffer contained 30 mM saccharose, 20 mM triethanol amine, 7 mM citric acid, and 1 mM PMSF, pH 4.6. The released glucose was enzymatically measured according to the method by Weil and Rausch (Planta 193 (1994), 430–437) in a coupled test with hexokinase and glucose-6-phosphate dehydrogenase.

EXAMPLE 7

Determination of Sugar Concentrations in Tissues

The concentrations of hexoses (glucose and fructose) in the tissue of the beet body were determined according to the method by Stitt et al. (Methods in Enzymology, 174 (1989), 518–552).

EXAMPLE 8

Production of Constructs for Plant Transformation with Wound-Induced Vacuolar Invertase (VIwit)

The VIwit DNA (2337 bp) is present in the pCR®2.1-TOPO® (Invitrogen) vector in "blunt end" cloned form. The VIwit cDNA (or a fragment thereof) is cut from this vector either by digestion with restriction endonucleases or is amplified using a polymerase chain reaction. The cloning in pBinAR is then performed using standard molecular biology methods (restriction digestion of the vector, purification of vector and insert, ligation of vector and insert, as well as transformation of the ligation formulation into a suitable bacteria strain).

FIG. 1 shows the construct for VIwit in antisense orientation under the control of the CaMV 35S promoter in pBinAR (pBin19 derivative).

Figure 2:
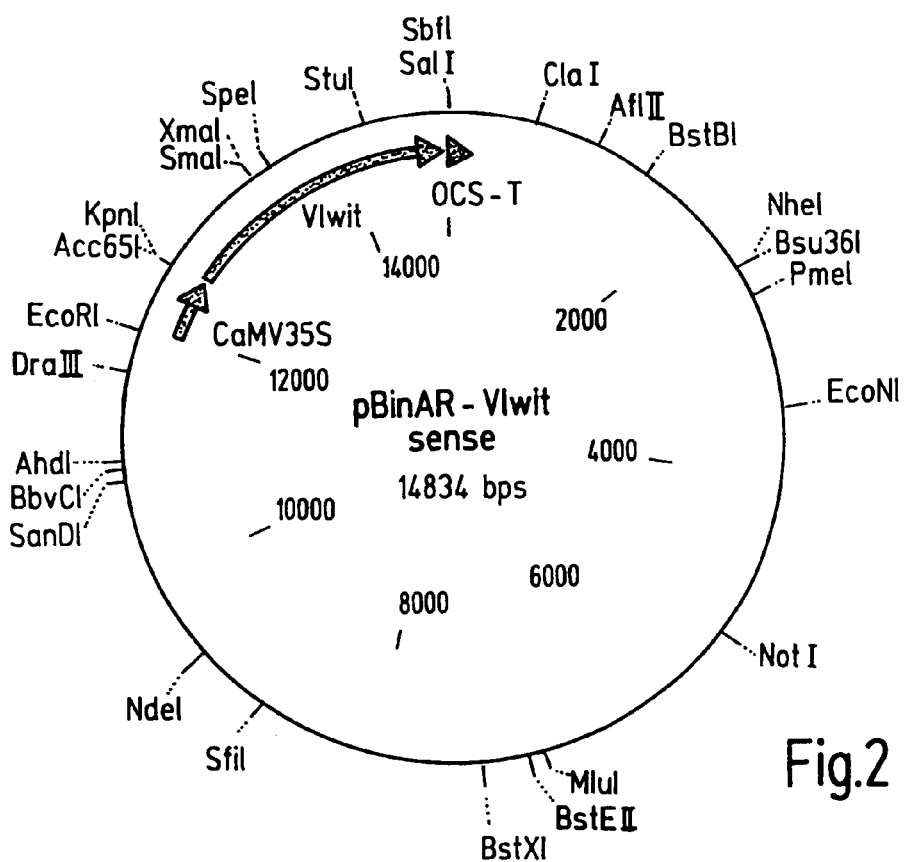
FIG. 2 shows a sense construct according to the invention with the nucleotide sequence according to the invention, the entire VIwit sequence cDNA being SEQ ID No. 2.

FIG. 2 shows a construct for VIwit in sense orientation in the same binary vector.

EXAMPLE 9

Transformation of *Agrobacterium Tumefaciens*

The DNA transfer into the agrobacteria was performed using direct transformation according to the method by Höfgen and Willmitzer (Nucl. Acids Res., 16 (1988), 9877). The plasmid DNA of transformed agrobacteria was isolated according to the method by Birnboim and Doly (Nucl. Acids Res., 7 (1979), 1513–1523) and was analyzed electrophoretically following suitable restriction cleavage.

EXAMPLE 10

Transformation of Sugar Beets to Obtain Transgenic Plants

About one month after the germination of sugar beet seeds in a green house, calli were induced according to the method described by Saunders et al. (J. Plant. Physiol., 124 (1986), 473–479). In the process, three to five centimeter long, young leaves were removed from each plant, disinfected, flushed three times with sterile water, and dried on sterile filter paper. Each leaf was then cut into pieces of approximately 0.25 cm$^2$, and the explants obtained in this way were incubated in Petri dishes for 30 days at 30° in the dark and were then transferred into culturing chambers. Four to ten weeks after culture start, white, brittle calli appeared on the leaf explants. Four to six weeks later, the calli were removed and cultivated in 250 ml Erlenmeyer flasks in liquid medium. After approximately two to three weeks, a cell suspension was obtained.

After approximately 3 weeks of cultivation, the cell suspensions were transformed. 10 ml of fresh medium was added to 10 ml of suspension medium. The suspension diluted in this way was distributed into four Petri dishes. From stock cultures of *Agrobacterium tumefaciens* strains that had been transformed with the created binary vectors, 50 µl were removed and cultivated in 2 ml LB medium that contained rifamicin and tetracycline. The cultures were stirred for two days at 200 rpm and 30° C. The strains were transferred to fresh medium and cultivated overnight under the previously described conditions. The plant cells were infected by adding 50 µl of an *Agrobacterium tumefaciens* strain from one of the Petri dishes containing the corresponding beet cells. The beet cells and bacteria were cultivated for three days in a culturing chamber in darkness. Then the bacteria were removed from the plan cells. The beet cells washed in this manner were cultivated in Petri dishes on a sheet of sterile Whatman paper and were then incubated for 15 days in the culturing chamber. After three to eight weeks, white calli appeared. After a certain time, sprouts and/or embryons developed from certain calli. As soon as the sprouts had started to develop leaves, these were rooted on medium that contained 1 mg/l of naphthalene acetic acid. After two to six weeks, roots appeared. Once roots had developed, the plants were acclimatized in the greenhouse in humus soil. After another three months, complete plants had developed.

EXAMPLE 11

Wound-induced Formation of VIwit in the Storage Root Tissue

Figure 3:
FIG. 3 shows the induction of VIwit mRNA (the entire VIwit cDNA sequence being SEQ ID No. 2) over time in injured storage root tissue of sugar beet tissue compared to the induction of PAL. For these experiments, 10 μg total RNA per track were loaded, and the uniform loading was verified by ethidium bromide staining and hybridization with an 18S RNA sample.
Figure 3:
Figure 3:
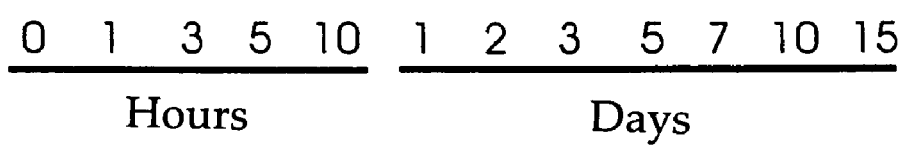

Storage root tissue of field-grown sugar beets was harvested 24 weeks after planting. To produce injured tissue, tissue cylinders with a diameter of 2 cm were cut with a set of razor blades from the cortex. The cuts were incubated in humid air at room temperature for various period ranging from one to 15 days. After three days, the tissue showed a slight browning, but no signs of bacterial or fungal infection. The tissue samples were obtained after different incubation times and studied for transcript quantities, the formation of VIwit, and the activity of VIwit. The RNA blot (FIG. 3) with gene-specific cDNA samples shows wound induction of VIwit. VIwit mRNA is induced approximately 24 hours after injury and reaches its maximum after approximately five days. The mRNA remains present over the entire period of 15 days. No signs of a non-specific mRNA breakdown could be determined, which shows that the cellular integrity was not negatively influenced. The transcript quantities of the phenylalanine ammonia lyase (PAL), a gene known for rapid induction after injury, were determined for comparison purposes. The PAL mRNA quantity increased three hours after injury and reached a maximum seven hours later. After five days, the PAL mRNA quantity decreased, whereby a level that is higher than that of uninjured tissue could be maintained, however.

Figure 4:
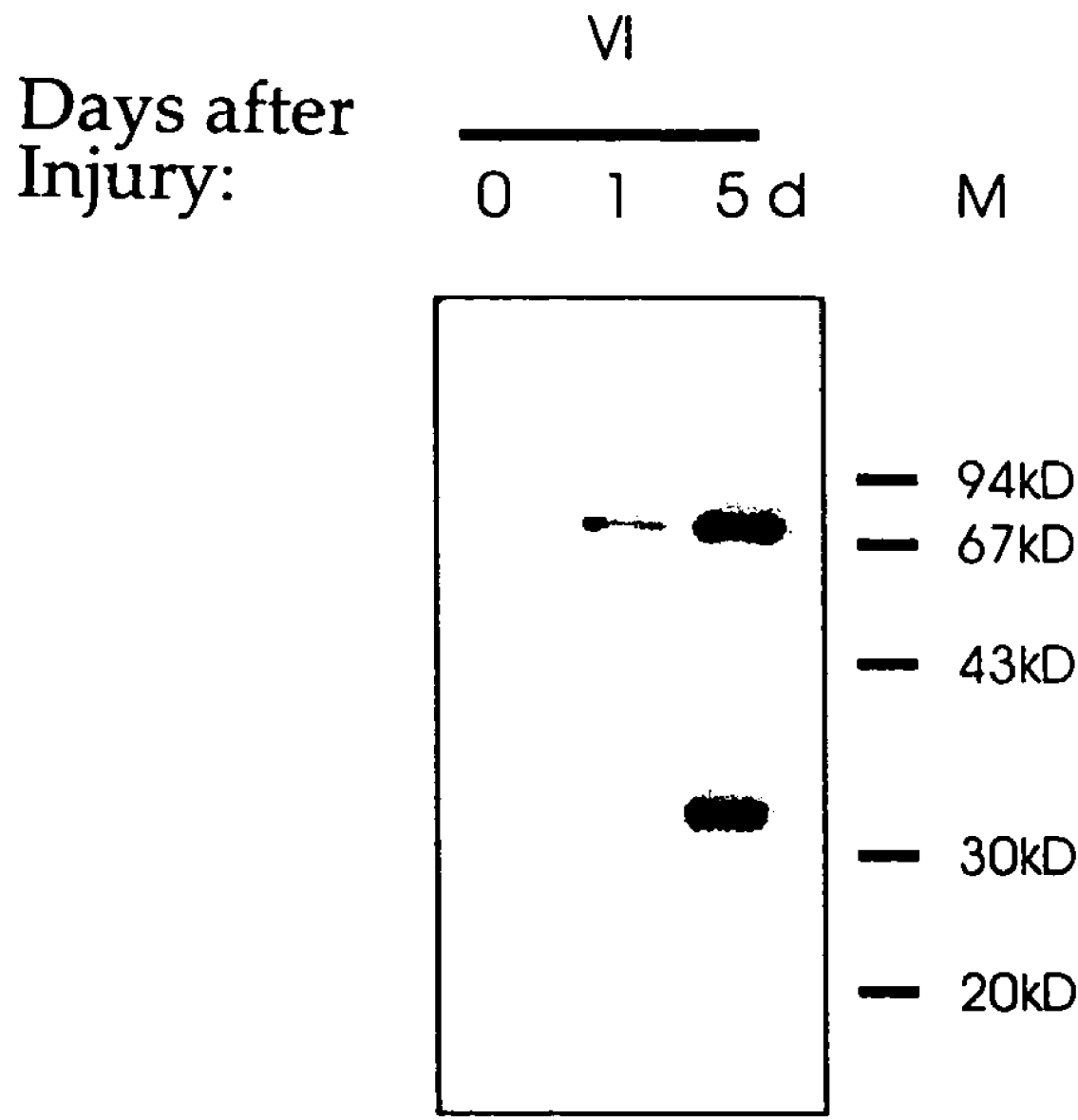
FIG. 4 shows the induction of VIwit protein, the entire VIwit cDNA sequence being SEQ ID No. 2, into injured sugar beet storage root tissue.

FIG. 4 shows the use of antisera against the central domain of VIwit. The immunoblots reflect the protein quantity of VIwit. The kinetics of the appearing of VIwit proteins correspond to the kinetics of the mRNA (see FIG. 3). Five days after injury, the immunoblot analysis with the VIwit antiserum shows an additional polypeptide with a molecular weight of approximately 33 kDa, which with all probability represents a fragment of VIwit.

Figure 5:
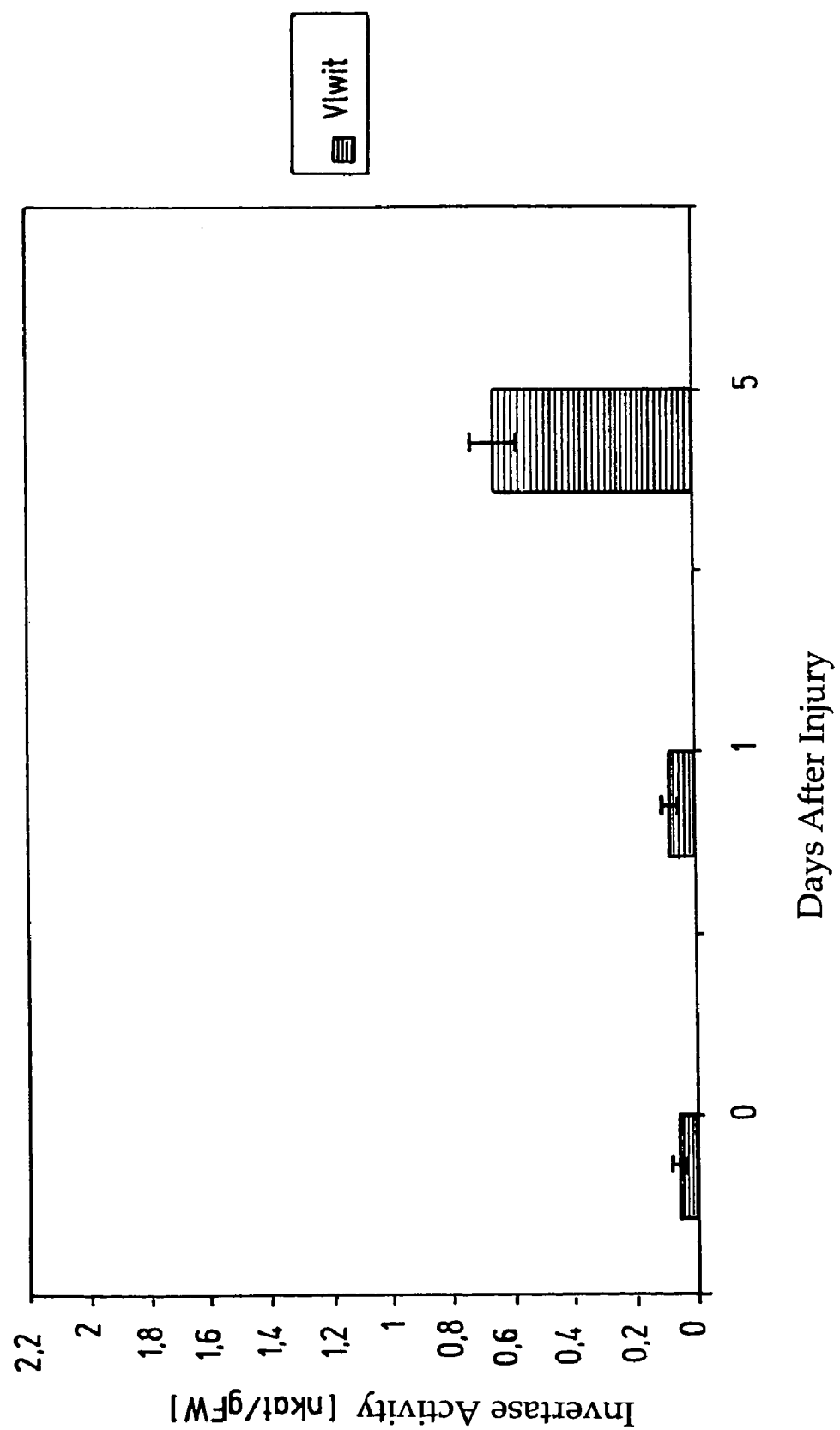
FIG. 5 shows the induction of VIwit (the entire VIwit cDNA sequence of which is a SEQ ID No. 2) enzyme activity over time in injured sugar beet storage root tissue. The data are stated as means + standard deviation from three different experiments; and, FIG. 6 shows an RNA blot with VIwit mRNA, the entire VIwit cDNA sequence being SEQ ID No. 2. In this figure, R: root, S: entire sprout; H: hypocotyls;; TR: tap root; YL: young leaf (50% of final size); OL: fully grown leaves; and F: flower. The plants were harvested 1, 4, 6, 8, 14, 16 and 66 weeks (W) after seeding.

The acidic invertase activities in soluble fractions of injured storage root tissue shown in FIG. 5 demonstrate good correlation with the data of FIG. 4. Within the first 24 hours, the vacuolar invertase activity increased by about 50%, whereby a seven-fold increase could be observed 4 days later. It could be demonstrated that VIwit is responsible for maintaining the increased hexose amounts during the wound reaction.

EXAMPLE 12

Expression of VIwit During Plant Development

Figure 6:
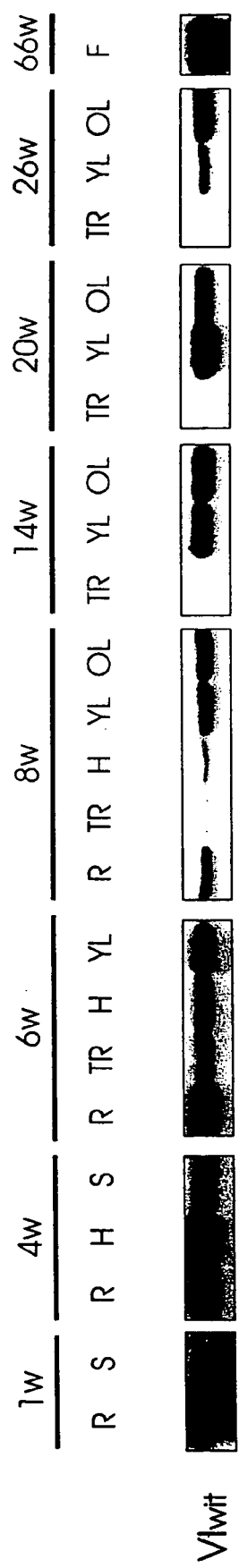

FIG. 6 shows the transcript quantities of VIwit in various plant organs during development (R root, S entire sprout, H hypocotyl, TR tap root, YL young leaf (50% of final size), OL fully grown leave, F flower). The plants were harvested 1, 4, 6, 8, 14, 20, 26, and 66 weeks (w) after seeding. 10 µg of total RNA were loaded per track and verified through identical loading with ethidium bromide staining and hybridization with an 18S RNA sample.

It could be shown that VIwit is expressed not only in the roots of seedlings, but especially also in leaves during the entire development.

The invention claimed is:

1. A purified nucleic acid molecule selected from the group consisting of:
   a) a nucleic acid molecule with the nucleotide sequence of SEQ ID No. 2;
   b) a nucleic acid molecule with the nucleotide sequence of SEQ ID No. 3;
   c) a nucleic acid molecule encoding the amino acid sequence of SEQ ID No. 4; and
   d) a nucleic acid molecule complementary to the nucleic acid molecule according to a), b), or c)
   wherein the nucleic acid molecule of a), b), or c) encodes a polypeptide having the biological activity of vacuolar wound-induced invertase.

2. The nucleic acid molecule according to claim 1, wherein the nucleic acid molecule is selected from the group consisting of a), b) and c), and is able to inhibit the expression of a plant vacuolar invertase in a plant host cell when expressed in said cell in antisense orientation.

3. A vector containing the nucleic acid molecule according to claim 1 operatively linked to at least one expression regulator element.

4. The vector according to claim 3, characterized in that the nucleic acid molecule is located in antisense orientation to at least one expression regulator element.

5. The vector according to claim 3, characterized in that the vector is present in the form of a plasmid, cosmid, phage, liposome, or virus.

6. A host cell, transformed with the nucleic acid molecule according to claim 1 or the vector according to claim 3.

7. The host cell according to claim 6, wherein said cell is a plant cell.

8. A transgenic plant, containing in its cells the nucleic acid molecule according to claim 1, or the vector according to claim 3, wherein expression of vacuolar invertase is suppressed and saccharose breakdown is reduced in said plant.

9. The transgenic plant according to claim 8, characterized in that one or more copies of the nucleic acid molecule, or the vector is/are integrated in a location/locations of the genome different from any native vacuolar invertase gene.

10. Propagation and harvesting material of a plant according to claim 8, wherein said material contains said nucleic acid molecule.

11. A method for reducing saccharose breakdown in a plant vacuole comprising inserting the nucleic acid molecule according to claim 1 a), b), c) or a fragment thereof into a plant cell; regenerating a plant from the plant cell; and selecting a transformed plant, wherein transcritpion of said nucleic acid molecule or fragment thereof results in co-suppression of the extension of vacuolar invertase in said plant, and saccharose breakdown in vacuoles is reduced compared to non-transgenic plants of the same species.

12. A method for reducing saccharose breakdown in a plant vacuole, comprising inserting the nucleic acid molecule according to claim 2 or a fragment thereof into a plant cell; regenerating a plant from the plant cell; and selecting a transgenic plant in which transcription of said nucleic acid molecule or fragment thereof inhibits expression of vacuolar invertase and causes a reduction of saccharose breakdown in plant vacuoles compared to non-transgenic plants of the same species.

13. The vector of claim 3, further comprising the complementary sequence of said nucleic acid molecule and an additional hairpin sequence, wherein the nucleic acid molecule, the complementary sequence and the additional hairpin sequence form a hairpin construct.

14. A method for reducing saccharose breakdown in a plant vacuole, comprising inserting the vector according to claim 3 or 13 into a plant cell; regenerating a transformed plant from the plant cell; whereby expression of vacuolar invertase is suppressed in the transformed plant and reduced saccharose breakdown is obtained in vacuoles within cells of the transformed plant.

15. The method according to claim 12, wherein the plant is a sugar beet.

16. The vector of claim 3, wherein the expression regulator element is tissue-specific or wound-induced expression regulator element.

17. The nucleic acid molecule according to claim 1, characterized in that it is a sugar beet DNA or RNA.

18. The method of claim 14, wherein the plant is a sugar beet.

19. An isolated nucleic acid molecule comprising the nucleotide sequence of SEQ ID NO:1 or the complement thereof.

* * * * *

UNITED STATES PATENT AND TRADEMARK OFFICE
CERTIFICATE OF CORRECTION

PATENT NO. : 7,157,280 B2  Page 1 of 1
APPLICATION NO. : 10/450606
DATED : January 2, 2007
INVENTOR(S) : Steffen Greiner et al.

It is certified that error appears in the above-identified patent and that said Letters Patent is hereby corrected as shown below:

On the title page:

Item (73) Please delete "Südzucker Aktiengesellschaft", and insert --Südzucker Aktiengesellschaft Mannheim/Ochsenfurt--

Signed and Sealed this

Twenty-third Day of September, 2008

JON W. DUDAS
*Director of the United States Patent and Trademark Office*

SEQUENCE LISTING

<160> NUMBER OF SEQ ID NOS: 10

<210> SEQ ID NO 1
<211> LENGTH: 686
<212> TYPE: DNA
<213> ORGANISM: Beta vulgaris

<400> SEQUENCE: 1

```
atgaagcctg atcaatggta tgatataaat ggtgtttgga cagggtccgc tacgatcttg      60
ccagatggca aaatcatgat ggtctacact ggtgacactg ataaatttgt acaagtccaa     120
aatttggcat accctgctaa cttatcggat ccattacttc ttgattgggt caaatacccg     180
ggtaatcctg ttttgacccc accagaggga atcggagcta agattttcg ggatccgacg      240
actgcatggg tggggcccga tgggatttgg aggcttatta tcgggtcgaa aacgggtaca     300
acaggtattt cactagtgta caagaccaag gattttaaga cttatgagct agagagtaac     360
ctccatgcag ttccgggtac gggtatgtgg gaatgtgtgg attttaccc ggtgtcgatc      420
acgggtcaaa atgggttgga tacctcggct tatgggtcgg gtatgaagca cttgttgaag     480
gctagtttgg atgataataa gcaagatcat tatgcattgg ggacttatga tatgacaact     540
caaacttgga cacctgataa cccggatatg gatgtgggtc ttgggttgag actggattat     600
ggtaaatatt atgcgtctaa gacatttttt gaccagaata agcaaaggag gattttgtgg     660
ggttgggttg gtgagtctga cagtga                                          686
```

<210> SEQ ID NO 2
<211> LENGTH: 2337
<212> TYPE: DNA
<213> ORGANISM: Beta vulgaris

<400> SEQUENCE: 2

```
aaatccaacc ttgacaacac ctccactacc ttcccccatt ttctttttta tctatttaga      60
tctctctcct cttttctctct cttcttatcc tctctctttc tctctccttc ttcaacgacg    120
aaaaatatgg cttcctactt ctctcccttc gcagacctag aaaacaatga gcccctcctc    180
cgggcccata tgacccagt ttcagcccaa ccggaacccg aaagcccaac ccaacggccc      240
attaaggaa tcgcgatact cagcttgtct ttcatgctta ctatcatt aatggcgatc        300
atatataacg ggcagcctgc ccttctgccc gtatcattgt cgtcggagaa taccgaaacg    360
gcgtcgtcgg agaaggtggg accagcggtt gtttctagag ggaaaaaaga aggcgtgtcg    420
gagaagattt caagagtagg agaaagtggt atttcgtttg cgtggactaa tgatatgttg    480
aggtggcaac gaagtggggtt ccattttcag ccggagaaaa attggatgaa tgatcctaat    540
ggtccactgt attacaaggg attctatcat ctatttttatc agtataaccc tgattcagct    600
gtttggggga acattacatg gggccatgca atttcaacgg acctgattca ctggaaatat    660
ctcccaatct caatgaagcc tgatcaatgg tatgatataa atggtgtttg gacagggtcc    720
gctacgatct tgccagatgg caaaatcatg atggtctaca ctggtgacac tgataaattt    780
gtacaagtcc aaaatttggc ataccctgct aacttatcgg atccattact tcttgattgg    840
gtcaaatacc cggtaatcct gttttgaccc ccaccagagg gaatcggagc taagattttt    900
cgggatccga cgactgcatg gtggggccc gatgggattt ggaggcttat tatcgggtcg    960
aaaacgggta acaggtat ttcactagtg tacaagacca aggattttaa gacttatgag   1020
ctagagagta acctccatgc agttccgggt acgggtatgt gggaatgtgt ggattttac     1080
ccggtgtcga tcacgggtca aaatggttg gatacctcgg cttatgggtc gggtatgaag    1140
cacttgttga aggctagttt ggatgataat aagcaagatc attatgcatt ggggacttat    1200
gatatgacaa ctcaaacttg gacacctgat aacccggata tggatgtggg tcttgggttg   1260
agactggatt atggtaaata ttatgcgtct aagacatttt ttgaccagaa taagcaaagg    1320
```

| | |
|---|---|
| aggattttgt ggggttgggt tggtgagaca gatactgagg ctgatgattt gttgaaggga | 1380 |
| tgggcttctt tgcagacaat tccaagggtt gtgacctatg atgcaaagac cggaaccaac | 1440 |
| atacttcaat ggccagtaaa agaagtggag tccttgagaa cagacagcag agaatatgat | 1500 |
| aatcttttgt tacaaccagg atccatcatt aaccttgaca taacctctgg tgcacagttg | 1560 |
| gatataagtg ctgaatttgt ggtggatcaa gaggcgctga atcaacagt aggagatgat | 1620 |
| gtgatcaaca attgcagtgc tgcagctgtt aggcaggctt gggcccgtt tgggcttttg | 1680 |
| gttttggctg atgagtccct ctccgaatta actcctattt acttttacat tgctaaggcc | 1740 |
| tctgatggaa ctgttaaaaa ttggttttgc actgatcaat caaggtcatc aaaggcttct | 1800 |
| agtgttgaca aacaaatata tggaggacca gttcctgttc tcgaaggtga aaagtatagc | 1860 |
| atgcggttac ttgttgatca ttcaataatt gaagcttttg gtcaaggagg gcgtacatgc | 1920 |
| ataacctcta gaatatatcc aacaaaggca atcaacggaa atgccaaggt tttcatcttc | 1980 |
| aataatgcta ctgattcaag tgtcacagcc tctgtcaaaa tctgggaatt ggactcaatt | 2040 |
| aatctttctc cctacatttt ttgatttgat tgttgaattt ttttttattt attgaattgt | 2100 |
| attaatatga tgtactatat atttgtacca attcaaattc taaggggaaa gaaaatgtct | 2160 |
| ttcttttctg ggtgggggt ggggagtgt tgtattgttt gagtcacttc attgtgttaa | 2220 |
| tggttgattt gaggccatga aaataggaat atagatttga tgaataaatg agaattgtaa | 2280 |
| caagggcatg aagagaaatg gaactatgac aaatttaatg gaaaaaaaaa aaaaaaa | 2337 |

```
<210> SEQ ID NO 3
<211> LENGTH: 1938
<212> TYPE: DNA
<213> ORGANISM: Beta vulgaris

<400> SEQUENCE: 3
```

| | |
|---|---|
| atggcttcct acttctctcc cttcgcagac ctagaaaaca atgagcccct cctccgggcc | 60 |
| cataatgacc cagtttcagc ccaaccggaa cccgaaagcc caacccaacg gcccattaag | 120 |
| ggaatcgcga tactcagctt gtctttcatg cttatactat cattaatggc gatcatatat | 180 |
| aacgggcagc ctgcccttct gcccgtatca ttgtcgtcgg agaataccga aacggcgtcg | 240 |
| tcggagaagg tgggaccagc ggttgtttct agagggaaaa agaaggcgt gtcggagaag | 300 |
| atttcaagag taggagaaag tggtatttcg tttgcgtgga ctaatgatat gttgaggtgg | 360 |
| caacgaagtg ggttccattt tcagccggag aaaaattgga tgaatgatcc taatggtcca | 420 |
| ctgtattaca agggattcta tcatctattt tatcagtata ccctgattc agctgtttgg | 480 |
| gggaacatta catggggcca tgcaatttca acggacctga ttcactggaa atatctccca | 540 |
| atctcaatga agcctgatca atggtatgat ataaatggtt tttggacagg gtccgctacg | 600 |
| atcttgccag atggcaaaat catgatggtc tacactggtg acactgataa atttgtacaa | 660 |
| gtccaaaatt tggcatacc tgctaactta tcggatccat tacttcttga ttgggtcaaa | 720 |
| taccccgggta atcctgtttt gaccccacca gagggaatcg gagctaaaga ttttcgggat | 780 |
| ccgacgactg catgggtggg gcccgatggg atttggaggc ttattatcgg gtcgaaaacg | 840 |
| ggtacaacag gtatttcact agtgtacaag accaaggatt ttaagactta tgagctagag | 900 |
| agtaacctcc atgcagttcc gggtacgggt atgtgggaat gtgtgatttt ttacccggtg | 960 |
| tcgatcacgg gtcaaaatgg gttggatacc tcggcttatg ggtcgggtat gaagcacttg | 1020 |
| ttgaaggcta gtttgatga taataagcaa gatcattatg cattggggac ttatgatatg | 1080 |
| acaactcaaa cttggacacc tgataaccccg gatatggatg tgggtcttgg gttgagactg | 1140 |

```
gattatggta aatattatgc gtctaagaca ttttttgacc agaataagca aaggaggatt   1200
ttgtggggtt gggttggtga gacagatact gaggctgatg atttgttgaa gggatgggct   1260
tctttgcaga caattccaag ggttgtgacc tatgatgcaa agaccggaac caacatactt   1320
caatggccag taaaagaagt ggagtccttg agaacagaca gcagagaata tgataatctt   1380
ttgttacaac caggatccat cattaacctt gacataacct ctggtgcaca gttggatata   1440
agtgctgaat ttgtggtgga tcaagaggcg ctgaaatcaa cagtaggaga tgatgtgatc   1500
aacaattgca gtgctgcagc tgttaggcag gctttgggcc cgtttgggct tttggttttg   1560
gctgatgagt ccctctccga attaactcct atttactttt acattgctaa ggcctctgat   1620
ggaactgtta aaaattggtt ttgcactgat caatcaaggt catcaaaggc ttctagtgtt   1680
gacaaacaaa tatatggagg accagttcct gttctcgaag gtgaaaagta tagcatgcgg   1740
ttacttgttg atcattcaat aattgaagct tttggtcaag gagggcgtac atgcataacc   1800
tctagaatat atccaacaaa ggcaatcaac ggaaatgcca aggttttcat cttcaataat   1860
gctactgatt caagtgtcac agcctctgtc aaaatctggg aattggactc aattaatctt   1920
tctccctaca tttttttga                                                 1938

<210> SEQ ID NO 4
<211> LENGTH: 645
<212> TYPE: PRT
<213> ORGANISM: Beta vulgaris

<400> SEQUENCE: 4

Met Ala Ser Tyr Phe Ser Pro Phe Ala Asp Leu Glu Asn Asn Glu Pro
  1               5                  10                  15

Leu Leu Arg Ala His Asn Asp Pro Val Ser Ala Gln Pro Glu Pro Glu
                 20                  25                  30

Ser Pro Thr Gln Arg Pro Ile Lys Gly Ile Ala Ile Leu Ser Leu Ser
             35                  40                  45

Phe Met Leu Ile Leu Ser Leu Met Ala Ile Ile Tyr Asn Gly Gln Pro
         50                  55                  60

Ala Leu Leu Pro Val Ser Leu Ser Ser Glu Asn Thr Glu Thr Ala Ser
 65                  70                  75                  80

Ser Glu Lys Val Gly Pro Ala Val Val Ser Arg Gly Lys Lys Glu Gly
                 85                  90                  95

Val Ser Glu Lys Ile Ser Arg Val Gly Glu Ser Gly Ile Ser Phe Ala
                100                 105                 110

Trp Thr Asn Asp Met Leu Arg Trp Gln Arg Ser Gly Phe His Phe Gln
            115                 120                 125

Pro Glu Lys Asn Trp Met Asn Asp Pro Asn Gly Pro Leu Tyr Tyr Lys
        130                 135                 140

Gly Phe Tyr His Leu Phe Tyr Gln Tyr Asn Pro Asp Ser Ala Val Trp
145                 150                 155                 160

Gly Asn Ile Thr Trp Gly His Ala Ile Ser Thr Asp Leu Ile His Trp
                165                 170                 175

Lys Tyr Leu Pro Ile Ser Met Lys Pro Asp Gln Trp Tyr Asp Ile Asn
            180                 185                 190

Gly Val Trp Thr Gly Ser Ala Thr Ile Leu Pro Asp Gly Lys Ile Met
        195                 200                 205

Met Val Tyr Thr Gly Asp Thr Asp Lys Phe Val Gln Val Gln Asn Leu
    210                 215                 220
```

-continued

```
Ala Tyr Pro Ala Asn Leu Ser Asp Pro Leu Leu Leu Asp Trp Val Lys
225                 230                 235                 240

Tyr Pro Gly Asn Pro Val Leu Thr Pro Pro Glu Gly Ile Gly Ala Lys
                245                 250                 255

Asp Phe Arg Asp Pro Thr Thr Ala Trp Val Gly Pro Asp Gly Ile Trp
            260                 265                 270

Arg Leu Ile Ile Gly Ser Lys Thr Gly Thr Thr Gly Ile Ser Leu Val
        275                 280                 285

Tyr Lys Thr Lys Asp Phe Lys Thr Tyr Glu Leu Glu Ser Asn Leu His
    290                 295                 300

Ala Val Pro Gly Thr Gly Met Trp Glu Cys Val Asp Phe Tyr Pro Val
305                 310                 315                 320

Ser Ile Thr Gly Gln Asn Gly Leu Asp Thr Ser Ala Tyr Gly Ser Gly
                325                 330                 335

Met Lys His Leu Leu Lys Ala Ser Leu Asp Asp Asn Lys Gln Asp His
            340                 345                 350

Tyr Ala Leu Gly Thr Tyr Asp Met Thr Thr Gln Thr Trp Thr Pro Asp
        355                 360                 365

Asn Pro Asp Met Asp Val Gly Leu Gly Leu Arg Leu Asp Tyr Gly Lys
    370                 375                 380

Tyr Tyr Ala Ser Lys Thr Phe Phe Asp Gln Asn Lys Gln Arg Arg Ile
385                 390                 395                 400

Leu Trp Gly Trp Val Gly Glu Thr Asp Thr Glu Ala Asp Asp Leu Leu
                405                 410                 415

Lys Gly Trp Ala Ser Leu Gln Thr Ile Pro Arg Val Val Thr Tyr Asp
            420                 425                 430

Ala Lys Thr Gly Thr Asn Ile Leu Gln Trp Pro Val Lys Glu Val Glu
        435                 440                 445

Ser Leu Arg Thr Asp Ser Arg Glu Tyr Asp Asn Leu Leu Leu Gln Pro
    450                 455                 460

Gly Ser Ile Ile Asn Leu Asp Ile Thr Ser Gly Ala Gln Leu Asp Ile
465                 470                 475                 480

Ser Ala Glu Phe Val Val Asp Gln Glu Ala Leu Lys Ser Thr Val Gly
                485                 490                 495

Asp Asp Val Ile Asn Asn Cys Ser Ala Ala Val Arg Gln Ala Leu
            500                 505                 510

Gly Pro Phe Gly Leu Leu Val Leu Ala Asp Glu Ser Leu Ser Glu Leu
        515                 520                 525

Thr Pro Ile Tyr Phe Tyr Ile Ala Lys Ala Ser Asp Gly Thr Val Lys
    530                 535                 540

Asn Trp Phe Cys Thr Asp Gln Ser Arg Ser Ser Lys Ala Ser Ser Val
545                 550                 555                 560

Asp Lys Gln Ile Tyr Gly Gly Pro Val Pro Val Leu Glu Gly Glu Lys
                565                 570                 575

Tyr Ser Met Arg Leu Leu Val Asp His Ser Ile Ile Glu Ala Phe Gly
            580                 585                 590

Gln Gly Gly Arg Thr Cys Ile Thr Ser Arg Ile Tyr Pro Thr Lys Ala
        595                 600                 605

Ile Asn Gly Asn Ala Lys Val Phe Ile Phe Asn Asn Ala Thr Asp Ser
    610                 615                 620

Ser Val Thr Ala Ser Val Lys Ile Trp Glu Leu Asp Ser Ile Asn Leu
625                 630                 635                 640

Ser Pro Tyr Ile Phe
```

-continued

645

<210> SEQ ID NO 5
<211> LENGTH: 7564
<212> TYPE: DNA
<213> ORGANISM: Beta vulgaris
<220> FEATURE:
<221> NAME/KEY: misc_feature
<222> LOCATION: (1)
<223> OTHER INFORMATION: "n" means "a or g or c or t/u,
    unknown or other"
<220> FEATURE:
<221> NAME/KEY: misc_feature
<222> LOCATION: (3)
<223> OTHER INFORMATION: n = a or g or c or t/u, unknown or other
<220> FEATURE:
<221> NAME/KEY: misc_feature
<222> LOCATION: (6)
<223> OTHER INFORMATION: n = a or g or c or t/u, unknown or other
<220> FEATURE:
<221> NAME/KEY: misc_feature
<222> LOCATION: (13)
<223> OTHER INFORMATION: n = a or g or c or t/u, unknown or other
<220> FEATURE:
<221> NAME/KEY: misc_feature
<222> LOCATION: (15)
<223> OTHER INFORMATION: n = a or g or c or t/u, unknown or other
<220> FEATURE:
<221> NAME/KEY: misc_feature
<222> LOCATION: (22)
<223> OTHER INFORMATION: n = a or g or c or t/u, unknown or other
<220> FEATURE:
<221> NAME/KEY: misc_feature
<222> LOCATION: (29)
<223> OTHER INFORMATION: n = a or g or c or t/u, unknown or other
<220> FEATURE:
<221> NAME/KEY: misc_feature
<222> LOCATION: (42)
<223> OTHER INFORMATION: n 0 a or g or c or t/u, unknown or other
<220> FEATURE:
<221> NAME/KEY: misc_feature
<222> LOCATION: (53)
<223> OTHER INFORMATION: n = a or g or c or t/u, unknown or other
<220> FEATURE:
<221> NAME/KEY: misc_feature
<222> LOCATION: (59)
<223> OTHER INFORMATION: n = a or g or c or t/u, unknown or other
<220> FEATURE:
<221> NAME/KEY: misc_feature
<222> LOCATION: (1959)
<223> OTHER INFORMATION: n = a or g or c or t/u, unknown or other
<220> FEATURE:
<221> NAME/KEY: misc_feature
<222> LOCATION: (1965)
<223> OTHER INFORMATION: n = a or g or c or t/u, unknown or other
<220> FEATURE:
<221> NAME/KEY: misc_feature
<222> LOCATION: (2089)
<223> OTHER INFORMATION: n = a or g or c or t/u, unknown or other
<220> FEATURE:
<221> NAME/KEY: misc_feature
<222> LOCATION: (2241)
<223> OTHER INFORMATION: n = a or g or c or t/u, unknown or other
<220> FEATURE:
<221> NAME/KEY: misc_feature
<222> LOCATION: (62)
<223> OTHER INFORMATION: n= a or g or c or t/u, unknown or other

<400> SEQUENCE: 5
ncnagncatg tangntacca angtgattnt agttagctag ancgtaaaaa cantaaatng    60
tnggctaatc aagggttgtc agtcaaatgt attgattaat ggagttaata ataaagcatt   120
agatatgtac ttgatcatat actactatga acacacatgc accccttatt tatttaaccc   180
aatacaatat acttagaaaa tatctttcag tttaattgtt tttctccttt tcacactaaa   240

```
tatatactac tacaagtttg ttttattgca ccatgattca cgagctgccg ccaaacacgg    300
tcactatctt ccatgcttga cctggcccaa ttattgaagc tctattattt tcataactaa    360
gctgaattaa tgattatgt agaaaaatgg acaagatacc taatcatata ctccactaac     420
ctatcctttc tctaaatagt aagttaaaat ctcatatccc ctaaaaaaaa gttagaatct    480
tatatctttt gtgaggttag atctataatt tttttgaca tattataatg aaatgttttt     540
atttattctc ttattgatcc atgtcaatat ttaggtttgt aattttggt tttctcgatt     600 gacatataag tagttagatt gttgaaaaca aatgtttggc aaaactagca ttttagtag     660 ctgtagctat tggggtagt tgctagctgt ctactagtag ccgtcaatga tcaatgatta     720
aattagttgt ttaattagaa gtgtttgaca aaagtagctg ttggaataat aaaaccagag    780
taaatgatat ttattctaaa atgaaatgaa ctaaaacaat ttcatatgtt cgttcaatag    840
ttaaattcaa tatttatttt ttcaaagaag ttacacaaaa gagaggtata caaattttat    900
agctgctcaa aaaatgtat aaatctaaga aatattcag ccccaaaaa atttatatta       960 ccagttttaa ctagatactt gtaaaatata ttatctttaa aataaatatt taaattacat    1020
ctctgctatt gtaaaacaaa cattgaattg ccataaaata aaataattaa tatacagtaa    1080
aagggaaaaa aaacaaaaaa aatattggtt aataattcta cctcatgcta ttatatactc    1140
cctccgtttt ttttagatgt aacattggac ttttcacatt tgccgaggca caactttgac    1200
cgataatatc tccaattgta taaaagtaaa aattataaaa aatatatatt tggaaagtgt    1260
ataccatgac gaatcaaaca agatcccaca tgactatatt ttttcttatg tataaataac    1320
aattagtggt caaagtgtat tggatgaata gtgcccaaag tcaatatgtt acatctaaaa    1380
aaaaaacgga gggagtagtg tttatttgct agacgctacc tctaaatctc aaacgttact    1440
tgtagagttg tagtaacgtt ccacaatcgc tactcataat ctactccaac tgctacccgc    1500
tagtacaacc actaccttac caaacactca taattttagc gtttcaatct tgtccaaccg    1560
ttaaccgcta cctcaaatgc tagtgtcaaa taggaccaca tgtatatcga gactccatct    1620
attcacttca tgtatgctcc ataaaaaagt aagatgtaga ttagaaagag aagagcctaa    1680
aatagtagga ataaagaggt ggttgaacgt tgtataaaaa ctaaaaagga aatctcgtga    1740
aaagaagaaa atataagttg acacctaata aaaaaattat gtgagattga tatgctttaa    1800
gcatgataca tgtttatgat ctagtaacat cttttgagtt ttgaccaaaa ttatgatatt    1860
agtacaaatt acaaatcaag aaataaagta ctcgcacaag caataattgt ttagtagaaa    1920
acgagtggct agaaaagtta atcgcctttc taagttttna gttgnagagt tgtgggccaa    1980
taaaaaataa ctaggtgtga tggttagatc gatattgatt attgacagtg ctactataag    2040 tttgagggt tgggccccat cttggagatt ttctttgctg gttgggtgna tatgcttgct     2100
cacgtatttg tggaaccata caactacaag accacacagt tcgtttgttt tcttcctttt    2160
ttttcttaag tagtaaaaaa gagtaatcag tgttcttcat ttatctcaaa aagggatgtc    2220
gtgtcatgac actttatttg natactttat tttaaactaa aaacttgact tacttctata    2280
aaatagctga gtcggacact tgaacacccg tgtccgaaca tacactcaat ccgtgtctga    2340
gtaacatagg gaataatcga tttgaattat ataacctttt tgttgattaa tttttaataa    2400
aacaatattt caattattcc tgaataatac aattttacat cctatttact tttcgtgagt    2460
cagaataact taaaattcgt ctaaaatatt aattcttcac cagaggagta aggacataaa    2520
gataagggaa ggaaaaaatt gacgagttgg gaaatgtggc ttaccaaaca aaccgattat    2580
aaacatgtca aatccattaa aagcaaatat ccaaaaaaag tttcattatt caagaataat    2640
```

```
tgaaacattg acttattaaa atttaatcgg ctaaaggttg tattattgaa attcattatt      2700
cattagaatc ataaaaaaca actcaattaa aaaaaatatg ggcgttgact ataatttctt      2760
ggatcaaaac agaaaatcaa ccaaattaat aaatattttg atcaaacctg aattggccaa      2820
atttgaccat atcagaaaac cctgataata tgataatatg attggggatg ccatgggtcg      2880
ggattttggg cggttcatc aacacctaga ccccagtttt agatattttt gatgtggatc       2940
cagatctggc ttgaaacccc attgtgtcta aaatctcaaa tctataccta ttgggtctag      3000
cgggtcctga gctaaaaatg gggttttaag atattttttct attatttat ggtctgttga      3060 tcatttaata tttatatatt ttttctcaaa attatattca tataacgaag ttaacgctta     3120
acgcgactac tatttaaacc tacttcagtt caaaagttta atacacgact ataaaaattc      3180
catgacctta aagatgctta gataagtact ctcatatata catacacttt agtagattag      3240
taattatttt taaaattcta attattaatt ctccttcatt gcatcattaa cttcaatttt      3300
cttagaataa agagacttac ggtggtgagc atgtaaggtc ctgttctttt ggacttattt      3360
tcagtttaat ttagtttaat tcagtttagt ttttatctac aattcagttt ctctcatttc      3420
agatcaattt ctctcattgc aaaataacgg ggcctaagtt gtattttgca attttatata      3480 tttatttat gaaaaatgg atccatgggt tggatctgga gtgtatctaa gtccgacctc        3540
attattcatg aacctagatc cgacctagga aaatttgaac cttgatttga catggacaca      3600
tagggtctaa aaaagatccg gactcttaaa aatgggtgg gtccgacagg gtttgagtca      3660
ggtcttagat tcattgtcat tcccaattat gaagaagctt cttgttaatc ttgtctttgt      3720
tggacttaaa catcatatgt attgttagaa tgttagattt gagaaaattc gttgatcttg      3780
gagtgatatc attgatcgat gtagaagagg ttacaaagtc tcagtcctaa ccgtgttaga      3840
aattttggaa tgataaggat aatctataca caattattcc aaatgtatgc aaaactatat      3900
actaaatatt ttctctatca tatatgttta ggattgtcta taaataacta tattttgatg      3960
acttattatt tgggaatgta ttttatggat ttatctcgat ggtgttatat atatatatat      4020
atatatatac tatgatctta ttcatatata attcaatatg aaattatata gaacttgact      4080
aaccaaacct aatataccac tttactcata attgttgaac ttatttggac tttactaatt      4140
ccttgttaaa caattatgag tttctaagta tctctagaaa gttaaaagta tagctactta      4200
ttattgcatg caagaaactt aattccaacc ttttgttaaa aaaaaaaaaa acacttaaaa      4260
gaaatccact ccttaatgat tatgtggaat tgtggattat ggataagaca tccacacctt      4320
tatgactatg tggattatgg ataaaacatt cacaataact tgattattat gatgttattg      4380
catttatttc aataaagtac tagttattag attcgggcta tgcttcgggt aagaaaaaat      4440
tttcattatt aatataataa tttatgataa taacactaaa tacaacttag cctagtggct      4500
aaaactttaa tatatatgct tgagttctcg tctttctcat aacgtaatag gttaaatgtt      4560
cctaaattta acggtatact tatctagttt atacagtacg ttttctgtt ataaatccac       4620 cacatagatt gagatttatg tgaataaaaa gaagacatag attgagagag acagtcattt      4680 ctacttttg atgtgaatca catgggataa atataaatct ttaatcatga aaccatagc        4740 tgatagcacg aatgtctcat ggactgtgga catcttacct gcttctttgc cacaattttt      4800
ttctcgactt gtggttacca atctgccaac cggggccttt atcttttata ctttttgtta     4860
tctgtgcacc acatgctcaa taagttaatt cctcaagatg ctgatctcaa aacaaataat      4920
aattaataat tagaaatgca agaagctgaa cacaatgatt tgagaagttt attagattta      4980
```

```
tttcaatatt gagaactcgt ttggttgtac ttgggaagtt gatttcccat gattttcact       5040
ttcatgaaat ttaacttcct aggaagtgag taaaattgtt tgataggcta tgggaagatg       5100
gaattcccat aggaagtggc acttacctag gagaattagg tgcgcaactt cccccattat       5160
gtgggaaata gaactttcta ggaagttcca cttcctatgc tctagttaaa caaacatcta       5220
cttatacttg tacttccttg aaacttgcaa tcaggaccgt ctcataaaat taggggcctg       5280
tgctaaatta aattataaaa attaattttt ttggtgaata ggaagagatg ggagaatcat       5340
taatgatctt ttttggagaa taggaggaga agaaacacca aacagtaatt tctttaagtt       5400
tgcattcaac attacacttt ataaaatttg aaagaaatac tttgtaatta gagttagctt       5460
tttttcccct taggaggata actaatagaa tcaggctact tatattttgg ggccctgtgc       5520
agttgctcac cctacacata gccttagccg cctttgcttg caattcctag gcaattggat       5580
gtcaaccaaa caaggcatga atatttaatt tgtagttgac gtgatgggta tagtagtgtc       5640
atcacatttc atttcgtatt tttgaattac aaggatcaaa tttggccttt tgagattcat       5700
ttgagaaatt ccccttattc ctccttaagc gagcctcctt gtaaattgta actaatacaa       5760
tttgaagcta tcaattaaaa taagaactgg agggacaaaa atgtaatata gcctcaccgt       5820
ctaagtaatt tagactctgc ctctccttt tagttaacac ggtttgattt tcaaatgtca       5880
atacacactt aaaatattat tatcattaat tatcgattag taaaactaca taaaattgat       5940
attatgaaaa tcttattgaa ataaatccaa catcgtacag aataatactc tctccgtcct       6000
aaaataaatg aaacactttt tttttttttt tatgtattag cttttgagg gaaactattt       6060 catttatttc ataatgaaag ttgttttgtt tttactatat acttcctctg tttctaaata       6120
agtgcaaaac ttcttgtttt cacgtttgcc aatgcattat tttaaccgtt aatatcttca       6180
attatcaata agtaaaaatt ataaaaagtt gatattaaaa aaattcacat tcagacgaat       6240
ctaacaagat cccacatgac tatgtttttc ctaaaatgta aatcaccaaa gctaattaaa       6300
gtttaaactg tgaatagtaa acactatgca aatgttgcac ttattttgaa acggaggaag       6360
tattactcaa aaaaaaaatt agcgtgggtt gtatgaataa tacaaggtgg aagtacaaat       6420
atattaaagt gaataaatta gatgtttttt ttattgataa agtacaaatt gcatgcttgc       6480
aggtccactg tattacaagg gattctatca tctatttat cagtataacc ctgattcagc       6540
tgtttggggg aacattacat ggggccatgc aatttcaacg gacctgattc actggaaata       6600
tctcccaatc tcaatgaagc ctgatcaatg gtatgatata aatggtgttt kgacagggtc       6660
cgctacgatc ttgccagatg gcaaaatcat gatggtctac actggtgaca ctgataaatt       6720
tgtacaagtc caaaatttgg catacccctg taacttatcg gatccattac ttcttgattg       6780
ggtcaaatac ccgggtaatc ctgttttgac cccaccagag ggaatcggag ctaaagattt       6840
tcgggatccg acgactgcat gggtgggcc cgatgggatt tggaggctta ttatcgggtc       6900
gaaaacgggt acaacaggta tttcactagt gtacaagacc aaggatttta agacttatga       6960
gctagagagt aacctccatg cagttccggg tacgggtatg tgggaatgtg tggattttta       7020
cccggtgtcg atcacgggtc aaaatgggtt ggatacctcg gcttatggtc ggtatgaa        7080 gcacttgttg aaggctagtt tggatgataa taagcaagat cattatgcat tggggactta       7140
tgatatgaca actcaaactt ggacacctga taacccggat atggatgtgg gtcttgggtt       7200
gagattggat tatggtaaat attatgcgtc taagacattt tttgaccaga ataagcaaag       7260
gaggattttg tggggttggg ttggagagac agatactgag gctgatgatt tgttgaaggg       7320
atgggcttct ttgcaggtat aatacttcat cctttgtcct tatcatttac ataatcacgt       7380
```

```
cattagttag ataaatacta tacacccaaa gcgtggatta tgcactaggg tgcagttgga    7440
tagcgtggat tatgcactag gatgtagttg gatatgctca gctgaactga gcccagtcca    7500
aatgccccgt atgtcacctt tgatataaaa attttgaatg atcttataaa gagtagcaca    7560
cccg                                                                 7564
```

<210> SEQ ID NO 6
<211> LENGTH: 284
<212> TYPE: PRT
<213> ORGANISM: Beta vulgaris
<220> FEATURE:
<221> NAME/KEY: UNSURE
<222> LOCATION: (56)
<223> OTHER INFORMATION: Xaa = unknown

<400> SEQUENCE: 6

```
Pro Leu Tyr Tyr Lys Gly Phe Tyr His Leu Phe Tyr Gln Tyr Asn Pro
 1               5                  10                  15

Asp Ser Ala Val Trp Gly Asn Ile Thr Trp Gly His Ala Ile Ser Thr
            20                  25                  30

Asp Leu Ile His Trp Lys Tyr Leu Pro Ile Ser Met Lys Pro Asp Gln
        35                  40                  45

Trp Tyr Asp Ile Asn Gly Val Xaa Thr Gly Ser Ala Thr Ile Leu Pro
    50                  55                  60

Asp Gly Lys Ile Met Met Val Tyr Thr Gly Asp Thr Asp Lys Phe Val
65                  70                  75                  80

Gln Val Gln Asn Leu Ala Tyr Pro Ala Asn Leu Ser Asp Pro Leu Leu
                85                  90                  95

Leu Asp Trp Val Lys Tyr Pro Gly Asn Pro Val Leu Thr Pro Pro Glu
            100                 105                 110

Gly Ile Gly Ala Lys Asp Phe Arg Asp Pro Thr Thr Ala Trp Val Gly
        115                 120                 125

Pro Asp Gly Ile Trp Arg Leu Ile Ile Gly Ser Lys Thr Gly Thr Thr
    130                 135                 140

Gly Ile Ser Leu Val Tyr Lys Thr Lys Asp Phe Lys Thr Tyr Glu Leu
145                 150                 155                 160

Glu Ser Asn Leu His Ala Val Pro Gly Thr Gly Met Trp Glu Cys Val
                165                 170                 175

Asp Phe Tyr Pro Val Ser Ile Thr Gly Gln Asn Gly Leu Asp Thr Ser
            180                 185                 190

Ala Tyr Gly Ser Gly Met Lys His Leu Leu Lys Ala Ser Leu Asp Asp
        195                 200                 205

Asn Lys Gln Asp His Tyr Ala Leu Gly Thr Tyr Asp Met Thr Thr Gln
    210                 215                 220

Thr Trp Thr Pro Asp Asn Pro Asp Met Asp Val Gly Leu Gly Leu Arg
225                 230                 235                 240

Leu Asp Tyr Gly Lys Tyr Tyr Ala Ser Lys Thr Phe Phe Asp Gln Asn
                245                 250                 255

Lys Gln Arg Arg Ile Leu Trp Gly Trp Val Gly Glu Thr Asp Thr Glu
            260                 265                 270

Ala Asp Asp Leu Leu Lys Gly Trp Ala Ser Leu Gln
        275                 280
```

<210> SEQ ID NO 7
<211> LENGTH: 23
<212> TYPE: DNA

```
<213> ORGANISM: Beta vulgaris
<220> FEATURE:
<221> NAME/KEY: misc_feature
<222> LOCATION: (6)
<223> OTHER INFORMATION: inosine

<400> SEQUENCE: 7
atggtnsckg aycrwtggta yga                                              23

<210> SEQ ID NO 8
<211> LENGTH: 23
<212> TYPE: DNA
<213> ORGANISM: Beta vulgaris

<400> SEQUENCE: 8
tcrstrtcwg wytchccaay cca                                              23

<210> SEQ ID NO 9
<211> LENGTH: 34
<212> TYPE: DNA
<213> ORGANISM: Beta vulgaris

<400> SEQUENCE: 9
gccgaatcga gctcataaat ggtgtttgga cagg                                  34

<210> SEQ ID NO 10
<211> LENGTH: 31
<212> TYPE: DNA
<213> ORGANISM: Beta vulgaris

<400> SEQUENCE: 10
gccgttagaa gcttagccga ggtatccaac c                                     31
```